US008039632B2

(12) United States Patent
Sørensen et al.

(10) Patent No.: US 8,039,632 B2
(45) Date of Patent: *Oct. 18, 2011

(54) 2-AMINIO-PYRIDINE DERIVATIVES AND THEIR USE AS POTASSIUM CHANNEL MODULATORS

(75) Inventors: Ulrik Svane Sørensen, Søborg (DK); Birgitte L. Eriksen, Farum (DK); Lene Teuber, Værlose (DK); Dan Peters, Malmö (SE); Dorte Strøbæk, Farum (DK); Tina Holm Johansen, Smørum (DK); Palle Christophersen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 38 days.

This patent is subject to a terminal disclaimer.

(21) Appl. No.: 12/514,532

(22) PCT Filed: Nov. 12, 2007

(86) PCT No.: PCT/DK2007/000498
§ 371 (c)(1),
(2), (4) Date: Jun. 16, 2009

(87) PCT Pub. No.: WO2008/058537
PCT Pub. Date: May 22, 2008

(65) Prior Publication Data
US 2010/0056584 A1   Mar. 4, 2010

Related U.S. Application Data

(60) Provisional application No. 60/865,673, filed on Nov. 14, 2006.

(30) Foreign Application Priority Data

Nov. 13, 2006 (DK) ................................ 2006 01475

(51) Int. Cl.
*C07D 213/72* (2006.01)
*A61K 31/44* (2006.01)
(52) U.S. Cl. ........................................ 546/304; 514/349
(58) Field of Classification Search .................. 546/304; 514/349
See application file for complete search history.

(56) References Cited

U.S. PATENT DOCUMENTS

| | | | |
|---|---|---|---|
| 3,075,984 A | 1/1963 | Surrey | |
| 6,605,623 B1 | 8/2003 | Ko et al. | |
| 7,186,834 B2 * | 3/2007 | Muller et al. | 546/1 |
| 2004/0029881 A1 | 2/2004 | Muller et al. | |
| 2008/0200529 A1 | 8/2008 | Sorensen et al. | |

FOREIGN PATENT DOCUMENTS

| | | |
|---|---|---|
| DE | 100 24 938 A1 | 11/2001 |
| JP | 2001-261651 A | 9/2001 |
| JP | 2003-238611 A | 8/2003 |
| WO | WO-2006/074991 A1 | 7/2006 |
| WO | WO 2007/110363 A1 | 10/2007 |

OTHER PUBLICATIONS

Faber et al., Clin. Exper. Pharmacol. Physiol. 34, 1077 (2007), p. 1080.*
Pedarzani et al., J.Biol.Chem. vol. 280, 4104 (2005)., p. 41410.*
Hardman et al., eds., "Goodman and Gilman's the Pharmacological Basis of Therapeutics." (9th edition) McGraw-Hill, 1996 p. 44, col. 2.*
Lewis, r., ed., "Hawley's Condensed Chemical Dictionary," 14th ed. John Wiley & Sons, 2002. Searchable on-line version . No pagination.*
Sailer et al., "Comparative immunohistochemical distribution of three small-conductance $Ca^{2+}$-activated potassium channel subunits, SK1, SK2, and SK3 in mouse brain", Molecular and Cellular Neuroscience, vol. 26, 2004, pp. 458-469.
Liégeois et al., "Modulation of small Conductance Calcium-Activated Potassium (SK) Channels: A New Challenge in Medicinal Chemistry", Current Medical Chemistry, XP009078229, vol. 10, 2003, pp. 625-647.
Takahashi et al., "Selective Preparation of Pyridines, Pyridones, and Iminopyridines from Two Different Alkynes via Azazirconacycles", Journal of American Chemical Society, XP009097790, vol. 124, No. 18, 2002, pp. 5059-5067.
Diversi et al., "Cobalt-Catalyzed Cyclo-Cotrimerization of Alkynes and Heterocumulenes", Journal of Molecular Catalysis, XP009097791, vol. 40, 1987, pp. 267-280.
Barbaro et al., "Periselectivity in Cycloadditions to Vinylmethylketene and Structurally Related Vinylketene Imines", Journal of Organic Chemistry, XP009097792, vol. 52, No. 15, 1987, pp. 3289-3296.
Meth-Cohn et al., "A Versatile New Synthesis of Quinolines and Related Fused Pyridines. Part 11. Conversion of Acylanilides into α-Iminopyridines", J. Chem. Soc. Perkin Trans, XP-002177755, vol. 1, 1983, pp. 2089-2092.
Chemical Abstract RN 764642-40-2, 2-[[4-[(phenylmethyl)imino]-1(4H)-pyridinyl]methyl]-benzonitrile, 2004.
Damavandy et al.; "Synthesis of •-Pyroneimine N-Oxide A Novel Nitrone with Electron Releasing Substituent"; J. Sci. I. R. Iran, vol. 8, No. 1, 1997, pp. 36-38.
Farber et al., Synthesis of N-Substituted 3-Hydroxy-2-methyl-4-pyridones and -pyridonimines, J. Heterocyclic Chem., 31, 1994, pp. 947-956.
Kibbe, "Handbook of Pharmaceutical Excipients", 3rd edition, 2000.
Michne et al., "Novel Inhibitors of Potassium Ion Channels on Human T Lymphocytes", J. Med. Chem. 1995, 38, pp. 1877-1883.
Wakselman, Fluorinated Organic Compounds: Synthesis and Biological Applications, Ann. Pharm Fr. 1999, 57 (2), pp. 108-115.
Wolff, "Burger's Medicinal Chemistry and Drug Discovery", 5th ed, New York John Wiley and Sons, 1996, vol. 1, pp. 975-977.
Office Action dated Jan. 3, 2011 in U.S. Appl. No. 12/514,284.

* cited by examiner

*Primary Examiner* — Janet Andres
*Assistant Examiner* — Heidi Reese
(74) *Attorney, Agent, or Firm* — Birch, Stewart, Kolasch & Birch, LLP

(57) ABSTRACT

This invention relates to novel 2-amino-pyridine derivative useful as modulators of small-conductance calcium-activated potassium channels (SK channels). In other aspects the invention relates to the use of these compounds in a method for therapy and to pharmaceutical compositions comprising the compounds of the invention.

7 Claims, No Drawings

2-AMINIO-PYRIDINE DERIVATIVES AND THEIR USE AS POTASSIUM CHANNEL MODULATORS

This application is the National Phase of PCT/DK2007/000498 filed on Nov. 13, 2007, which claims priority under 35 U.S.C. 119(e) to U.S. Provisional Application Ser. No. 60/865,673 filed on Nov. 14, 2006 and under 35 U.S.C. 119(a) to Patent Application Ser. No. PA 2006 01475 filed in Denmark on Nov. 13, 2006, all of which are hereby expressly incorporated by reference into the present application.

TECHNICAL FIELD

This invention relates to novel 2-amino-pyridine derivative useful as modulators of small-conductance calcium-activated potassium channels (SK channels). In other aspects the invention relates to the use of these compounds in a method for therapy and to pharmaceutical compositions comprising the compounds of the invention.

BACKGROUND ART

Three subtypes of small-conductance calcium-activated potassium channels (SK channels) have been cloned: SK1, SK2 and SK3 (corresponding to KCNN1-3 using the genomic nomenclature). The activity of these channels is determined by the concentration of free intracellular calcium ($[Ca^{2+}]_i$) via calmodulin that is constitutively bound to the channels. SK channels are tightly regulated by $[Ca^{2+}]_i$ in the physiological range being closed at $[Ca^{2+}]$ up to around 0.1 µM but fully activated at a $[Ca^{2+}]$ of 1 µM. Being selective for potassium, open or active SK channels have a hyperpolarizing influence on the membrane potential of the cell. SK channels are widely expressed in the central nervous system. The distribution of SK1 and SK2 show a high degree of overlap and display the highest levels of expression in neocortical, limbic and hippocampal areas in the mouse brain. In contrast, the SK3 channels show high levels of expression in the basal ganglia, thalamus and the brain stem monoaminergic neurons e.g. dorsal raphe, locus coeruleus and the ventral tegmental area (Sailer et al.: "Comparative immunohistochemical distribution of three small-conductance $Ca^{2+}$-activated potassium channel subunits, SK1, SK2 and SK3 in mouse brain", *Mol. Cell. Neurosci.* 2004 26 458-469). The SK channels are also present in several peripheral cells including skeletal muscle, gland cells, liver cells and T-lymphocytes.

The hyperpolarizing action of active SK channels plays an important role in the control of firing pattern and excitability of excitable cells. SK channel inhibitors such as apamin and quaternized anlogues of bicuculline have been demonstrated to increase excitability whereas the opener 1-EBIO is able to reduce electrical activity. In non-excitable cells where the amount of $Ca^{2+}$ influx via voltage-independent pathways is highly sensitive to the membrane potential an activation of SK channels will increase the driving force whereas a blocker of SK channels will have a depolarising effect and thus diminish the driving force for calcium.

Based on the important role of SK channels in linking $[Ca^{2+}]_i$ and membrane potential, SK channels are an interesting target for developing novel therapeutic agents.

A review of SK channels and SK channel modulators may be found in Liegeois, J.-F. et al.: "Modulation of small conductance calcium-activated potassium (SK) channels: a new challenge in medicinal chemistry", *Current Medicinal Chemistry* 2003 10 625-647.

Known modulators of SK channels suffer from being large, often positively charged, molecules or peptides (like apamin, scyllatoxin, tubocurarine, dequalinium chloride and UCL1684), or from having low potency (e.g. 1-EBIO and riluzole). Thus, there is a continued need for compounds with an optimized pharmacological profile. In particular, there is a great need for selective ligands, such as SK3 channel modulators.

SUMMARY OF THE INVENTION

In its first aspect, the invention provides 2-amino-pyridine derivatives of Formula I:

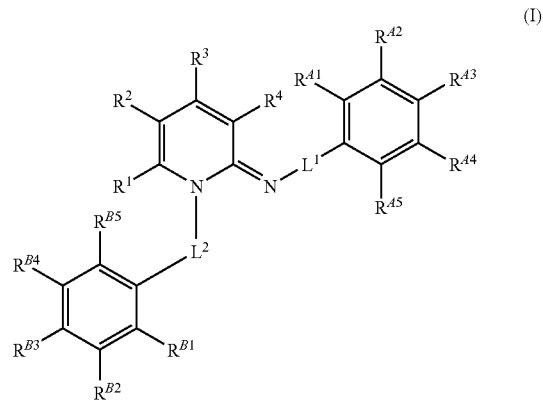

any of its tautomers, or any of its isomers or any mixture of its isomers, or a pharmaceutically acceptable salt thereof; wherein $L^1$ represents a linking group —[CR'R'']$_n$—; wherein R' and R'', independently of each other, represent hydrogen or alkyl; and n is 0, 1 or 2;

$L^2$ represents a linking group —[CR'''R'''']$_m$—; wherein R''' and R'''', independently of each other, represent hydrogen or alkyl; and m is 0, 1 or 2; and $R^1, R^2, R^3, R^4, R^{41}, R^{42}, R^{43}, R^{44}, R^{45}, R^{B1}, R^{B2}, R^{B3}, R^{B4}$ and $R^{B5}$, independently of each other, are selected from the group consisting of hydrogen, halo, trifluoromethyl, trifluoromethoxy, cyano, alkyl, hydroxy and alkoxy.

In its second aspect, the invention provides a pharmaceutical composition, comprising a therapeutically effective amount of the derivatives of the invention, including any isomers or any mixture of isomers, and pharmaceutically acceptable salts thereof, together with at least one pharmaceutically acceptable carrier, excipient or diluent.

In a further aspect, the invention provides the use of the 2-amino-pyridine derivatives of the invention, including any isomers or any mixture of isomers, and pharmaceutically acceptable salts thereof, for the manufacture of a pharmaceutical composition for the treatment, prevention or alleviation of a disease or a disorder or a condition of a mammal, including a human, which disease, disorder or condition is responsive to modulation of SK channels.

In a still further aspect, the invention relates to a method for treatment, prevention or alleviation of a disease or a disorder or a condition of a living animal body, including a human, which disorder, disease or condition is responsive to modulation of SK channels, which method comprises the step of administering to such a living animal body in need thereof a therapeutically effective amount of the 2-amino-pyridine derivatives of the invention, including any isomers or any mixture of isomers, and pharmaceutically acceptable salts thereof.

Other objects of the invention will be apparent to the person skilled in the art from the following detailed description and examples.

DETAILED DISCLOSURE OF THE INVENTION

2-Amino-Pyridine Derivatives

In its first aspect, the invention provides a 2-amino-pyridine derivative of Formula I:

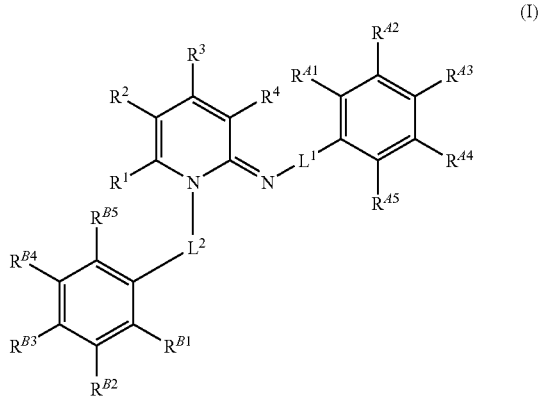

(I)

any of its tautomers, or any of its isomers or any mixture of its isomers, or a pharmaceutically acceptable salt thereof; wherein $L^1$ represents a linking group $—[CR'R'']_n—$; wherein R' and R'', independently of each other, represent hydrogen or alkyl; and n is 0, 1 or 2;

$L^2$ represents a linking group $—[CR'''R'''']_m—$; wherein R''' and R'''', independently of each other, represent hydrogen or alkyl; and m is 0, 1 or 2; and $R^1$, $R^2$, $R^3$, $R^4$, $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$, independently of each other, are selected from the group consisting of hydrogen, halo, trifluoromethyl, trifluoromethoxy, cyano, alkyl, hydroxy and alkoxy;

provided, however, at least one of $R^1$, $R^2$, $R^3$, $R^4$, $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$ is not hydrogen; and if n is 1 and m is 1, then $R^{A3}$ and $R^{B3}$ are not both bromo, or then $R^2$ is not methyl and $R^{B2}$ is not trifluoromethyl.

In a preferred embodiment the 2-amino-pyridine derivative of the invention is a compound of Formula I, wherein $L^1$ represents a linking group $—[CR'R'']_n—$; wherein R' and R'', independently of each other, represent hydrogen or alkyl; and n is 0, 1 or 2.

In a more preferred embodiment n is 0 or 1.
In another more preferred embodiment n is 1 or 2.
In an even more preferred embodiment n is 0.
In another more preferred embodiment n is 1.
In a third more preferred embodiment n is 2.
In a yet more preferred embodiment R' and R'' both represent hydrogen.

In another preferred embodiment the 2-amino-pyridine derivative of the invention is a compound of Formula I, wherein $L^2$ represents a linking group $—[CR'''R'''']_m—$; wherein R''' and R'''', independently of each other, represent hydrogen or alkyl; and m is 0, 1 or 2.

In a more preferred embodiment m is 0 or 1.
In another more preferred embodiment m is 1 or 2.
In an even more preferred embodiment m is 0.
In another more preferred embodiment m is 1.
In a third more preferred embodiment m is 2.
In a yet more preferred embodiment R''' and R'''' both represent hydrogen.

In a third preferred embodiment the 2-amino-pyridine derivative of the invention is a compound of Formula I, wherein $R^1$, $R^2$, $R^3$, $R^4$, $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$, independently of each other, are selected from the group consisting of hydrogen, halo, trifluoromethyl, trifluoromethoxy, cyano, alkyl, hydroxy and alkoxy.

In a more preferred embodiment $R^1$, $R^2$, $R^3$ and $R^4$, independently of each other, are selected from the group consisting of hydrogen, halo, trifluoromethyl, trifluoromethoxy, cyano, hydroxy and alkoxy; and $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$, independently of each other, are selected from the group consisting of hydrogen, halo, trifluoromethyl, trifluoromethoxy, cyano, alkyl, hydroxy and alkoxy.

In an even more preferred embodiment $R^1$, $R^2$, $R^3$ and $R^4$, independently of each other, are selected from the group consisting of hydrogen, halo, trifluoromethyl, trifluoromethoxy, cyano, alkyl, hydroxy and alkoxy; and $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$, independently of each other, are selected from the group consisting of hydrogen, trifluoromethyl, trifluoromethoxy, cyano, alkyl, hydroxy and alkoxy.

In a fourth preferred embodiment the 2-amino-pyridine derivative of the invention is a compound of Formula I, wherein $R^1$, $R^2$, $R^3$ and $R^4$ all represent hydrogen; and $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$, independently of each other, are selected from the group consisting of hydrogen, halo, trifluoromethyl, trifluoromethoxy, cyano, alkyl, hydroxy and alkoxy.

In a more preferred embodiment one of $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$, independently of each other, are selected from the group consisting of halo, trifluoromethyl, trifluoromethoxy, cyano, alkyl, hydroxy and alkoxy; and the remaining of $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$ all represent hydrogen.

In an even more preferred embodiment two of $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$, independently of each other, are selected from the group consisting of halo, trifluoromethyl, trifluoromethoxy, cyano, alkyl, hydroxy and alkoxy; and the remaining of $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$ all represent hydrogen.

In a still more preferred embodiment four of $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$, independently of each other, are selected from the group consisting of halo, trifluoromethyl, trifluoromethoxy, cyano, alkyl, hydroxy and alkoxy; and the remaining of $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$ all represent hydrogen.

In a yet more preferred embodiment four of $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$, independently of each other, are selected from the group consisting of halo, trifluoromethyl and trifluoromethoxy; and the remaining of $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$ all represent hydrogen.

In a further more preferred embodiment four of $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$ represent halo; and the remaining of $R^{A1}$, $R^{A2}$, $R^{A3}$, $R^{A4}$, $R^{A5}$, $R^{B1}$, $R^{B2}$, $R^{B3}$, $R^{B4}$ and $R^{B5}$ all represent hydrogen.

In a still further more preferred embodiment $R^{A2}$, $R^{A3}$, $R^{B2}$ and $R^{B3}$ represent halo; and $R^{A1}$, $R^{A4}$, $R^{A5}$, $R^{B1}$, $R^{B4}$ and $R^{B5}$ all represent hydrogen.

In a most preferred embodiment the 2-amino-pyridine derivative of the invention is
(3,4-Difluorobenzyl)-[1-(3,4-difluorobenzyl)-1H-pyridin-2-ylidene; or
[1-(3,4-Difluorobenzyl)-1H-pyridin-2-ylidene]-(3,4-difluorophenyl)amine;
or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contains of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

Alkoxy is O-alkyl, wherein alkyl is as defined above.

Pharmaceutically Acceptable Salts

The 2-amino-pyridine derivative of the invention may be provided in any form suitable for the intended administration. Suitable forms include pharmaceutically (i.e. physiologically) acceptable salts, and pre- or prodrug forms of the 2-amino-pyridine derivative of the invention.

Examples of pharmaceutically acceptable addition salts include, without limitation, the non-toxic inorganic and organic acid addition salts such as the hydro-chloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of a 2-amino-pyridine derivative of the invention include, without limitation, the sodium, the potassium, the calcium, the magnesium, the zinc, the aluminium, the lithium, the choline, the lysinium, and the ammonium salt, and the like, of a 2-amino-pyridine derivative of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the 2-amino-pyridine derivative of the invention include examples of suitable prodrugs of the substances according to the invention include compounds modified at one or more reactive or derivatizable groups of the parent compound. Of particular interest are compounds modified at a carboxyl group, a hydroxy group, or an amino group. Examples of suitable derivatives are esters or amides.

The 2-amino-pyridine derivative of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the 2-amino-pyridine derivatives of the present invention may contain one or more chiral centers, and that such compounds exist in the form of isomers.

Moreover, the 2-amino-pyridine derivative of the present invention may exist as enantiomers in (+) and (−) forms as well as in racemic forms (±). The racemates of these isomers and the individual isomers themselves are within the scope of the present invention.

The invention includes all such isomers and any mixtures thereof including racemic mixtures.

Racemic forms can be resolved into the optical antipodes by known methods and techniques. One way of separating the isomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The 2-amino-pyridine derivative of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Optical active compounds can also be prepared from optical active starting materials.

Labelled Compounds

The 2-amino-pyridine derivative of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{11}$C, $^{13}$C, $^{14}$C, $^{131}$I, $^{125}$I, $^{123}$I and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The 2-amino-pyridine derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The 2-amino-pyridine derivatives of the invention may be tested for their ability to modulate SK channels in vitro. Functional modulation can be determined by measuring the compound-induced change in SK current by the patch clamp technique as described in Strøbaek et al.: "Pharmacological characterization of small-conductance $Ca^{2+}$-activated K channels expressed in HEK293 cells", British Journal of Pharmacology (2000) 129, 991-999. From this type of measurements the potency of a given compound can be determined as e.g. $K_i$ or $IC_{50}$ values for blockers/inhibitors and $EC_{50}$ values for openers/activators. Similar data can be obtained from other patch clamp configurations and from channels expressed endogenously in various cell lines.

In one embodiment, the 2-amino-pyridine derivatives of the invention show selectivity for SK3 over SK1 and SK2. In a further embodiment, the compounds of the invention are positive SK channel modulators, such as positive SK3 channel modulators. In a still further embodiment, the compounds of the invention are negative modulators, such as negative SK3 channel modulators. In a special embodiment, the compounds of the invention are SK channel blockers, such as SK3 channel blockers.

Based on the activity observed in the patch clamp experiments, the compound of the invention is considered useful for the treatment, prevention or alleviation of a disease or a disorder or a condition of a mammal, including a human, which disease, disorder or condition is responsive to modulation of SK channels.

In a special embodiment, the 2-amino-pyridine derivatives of the invention are considered useful for the treatment, prevention or alleviation of absence seizures, agerelated memory loss, Alzheimer's disease, angina pectoris, arrhythmia, asthma, anxiety, ataxia, attention deficits, baldness, bipolar disorder, bladder hyperexcitability, bladder outflow obstruction, bladder spasms, brain tumors, cerebral ischaemia, chronic obstructive pulmonary disease, cancer, cardiovascular disorders, cognitive dysfunction, colitis, constipation, convulsions, coronary artery spasms, coronary hearth disease, cystic fibrosis, dementia, depression, diabetes type II, dysmenorrhoea, epilepsy, gastrointestinal dysfunction, gastroesophageal reflux disorder, gastrointestinal hypomotility disorders gastrointestinal motility insufficiency, hearing loss, hyperinsulinemia, hypertension, immune suppression, inflammatory bowel disease, inflammatory pain, intermittent claudication, irritable bowel syndrome, ischaemia, ischaemic hearth disease, learning deficiencies, male erectile dysfunction, manic depression, memory deficits, migraine, mood disorders, motor neuron diseases, myokymia, myotonic dystrophy, myotonic muscle dystrophia, narcolepsy, neuropathic pain, pain, Parkinson's disease, polycystic kidney disease, postoperative ileus, premature labour, psychosis, psychotic disorders, renal disorders, Reynaud's disease, rhinorrhoea, secretory diarrhoea, seizures, Sjogren's syndrome, sleep apnea, spasticity, sleeping disorders, stroke, traumatic brain injury, trigeminal neuralgia, urinary incontinence, urinogenital disorders, vascular spasms, vision loss, and xerostomia. In a more preferred embodiment the compounds of the invention are considered useful for the treatment, prevention or alleviation of depression, pseudodementia, Ganser's syndrome, obsessive compulsive disorder, panic disorder, memory deficits, memory loss, attention deficit hyperactivity disorder, obesity, anxiety, eating disorder, Parkinson's disease, parkinsonism, dementia, dementia of ageing, senile dementia, acquired immunodeficiency syndrome dementia complex, memory dysfunction in ageing, social phobia, drug addiction, drug misuse, cocaine abuse, tobacco abuse, alcoholism, pain, migraine pain, bulimia, premenstrual syndrome, late luteal phase syndrome, post-traumatic syndrome, chronic fatigue syndrome, premature ejaculation, erectile difficulty, anorexia nervosa, sleep disorders, autism, mutism, trichotillomania, narcolepsy, Gilles de la Tourettes disease, inflammatory bowel disease or irritable bowel syndrome.

In another more preferred embodiment the 2-amino-pyridine derivatives of the invention are considered useful for the treatment, prevention or alleviation of depression, pseudodementia, Ganser's syndrome, obsessive compulsive disorders, panic disorders, memory deficits, attention deficit hyperactivity disorder, obesity, anxiety, an eating disorder or Parkinson's disease.

In a third more preferred embodiment, the 2-amino-pyridine derivatives of the invention are considered useful for the treatment, prevention or alleviation of a respiratory disease, urinary incontinence, erectile dysfunction, anxiety, epilepsy, psychosis, schizophrenia, bipolar disorder, depression, amyotrophic lateral sclerosis (ALS), Parkinson's disease or pain.

In a fourth more preferred embodiment, the 2-amino-pyridine derivatives of the invention are considered useful for the treatment, prevention or alleviation of psychosis, schizophrenia, bipolar disorder, depression, epilepsy, Parkinson's disease or pain.

In a fifth more preferred embodiment, the 2-amino-pyridine derivatives of the invention are considered useful for the treatment, prevention or alleviation of pain, mild or moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury.

In a most preferred embodiment, the 2-amino-pyridine derivatives of the invention are considered useful for the treatment, prevention or alleviation of schizophrenia, depression or Parkinson's disease.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred 2-amino-pyridine derivatives of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of the 2-amino-pyridine derivative of the invention.

While a 2-amino-pyridine derivative of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the 2-amino-pyridine derivative of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be prepared by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of SK channels, and which method comprises administering to such a living animal body, including a human, in need thereof an effective amount of a 2-amino-pyridine derivative of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

General: The procedures represent generic procedures used to prepare compounds of the invention. Abbreviations used are as follows:

Ac: acetyl
Boc: t-butyloxycarbonyl
DME: 1,2-dimethoxyethane
DMF: N,N-dimethylformamide
DMSO: dimethylsulfoxide
Et: ethyl
eq: equivalents
HR-MS: high resolution mass spectrometry
LC-MS: Liquid chromatography mass spectrometry
MW: microwave
rt: room temperature
TEA: triethylamine Procedure A In the first step, 2-fluoropyridine, the required amine (1.5 eq) and TEA (1 eq) were dissolved in acetonitrile (under $N_2$) in a closed vial and heated to 170-225° C. for 0.5-4 hours using MW irradiation. After cooling to rt, aqueous saturated $NaHCO_3$ was added and the mixture extracted with EtOAc. The combined organic phases were dried ($MgSO_4$), filtered and concentrated in vacuo to give the crude product which was purified by preparative LC-MS or by column chromatography to give the desired N-substituted 2-aminopyridine.

In the second step, the N-substituted 2-aminopyridine and the required halide (1.5 eq) were dissolved in acetonitrile (under $N_2$) in a closed vial and heated to 120-170° C. for 60-180 min using MW irradiation. After cooling to rt, the crude product could be isolated upon aqueous basic work-up and subsequently purified by preparative LC-MS or, alternatively, by column chromatography and/or recrystallization to give the desired N,N'-disubstituted 2-aminopyridine.

An example of Procedure A, the preparation of (3,4-difluorobenzyl)-[1-(3,4-difluorobenzyl)-1H-pyridin-2-ylidene, is shown in Scheme 1.

Scheme 1

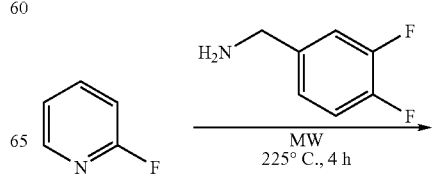

-continued

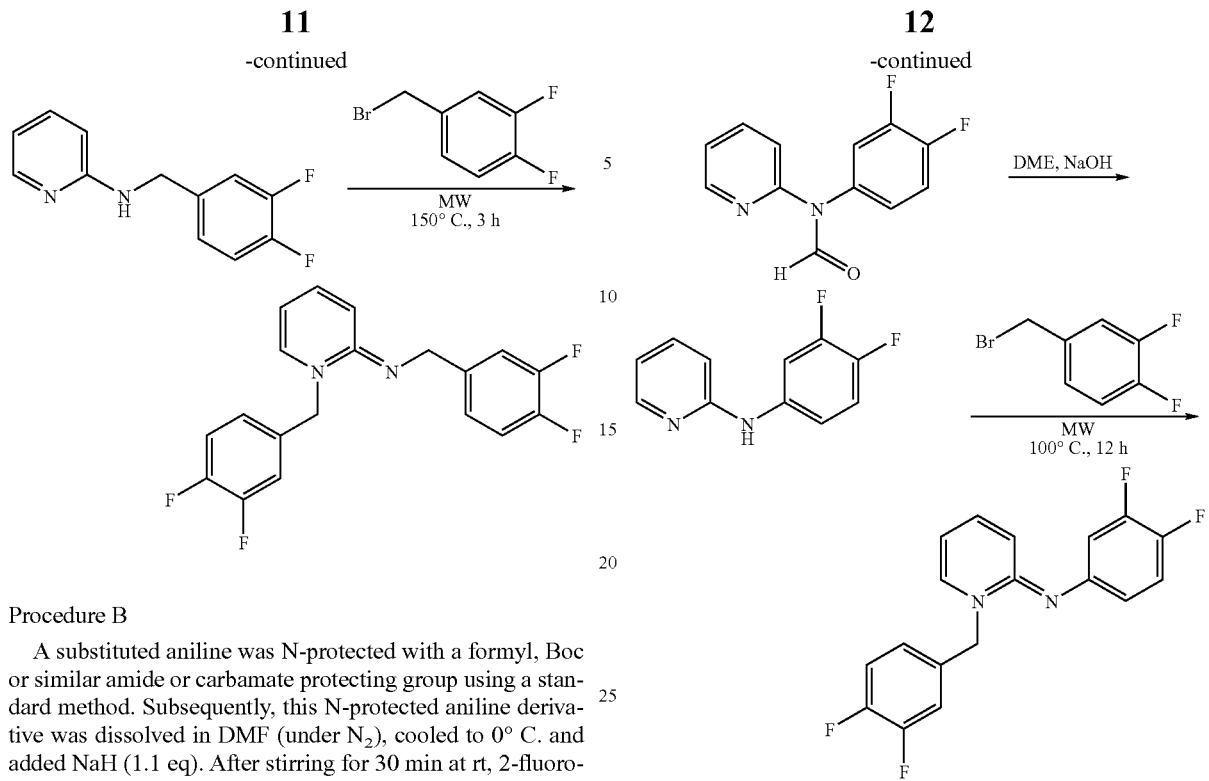

Procedure B

A substituted aniline was N-protected with a formyl, Boc or similar amide or carbamate protecting group using a standard method. Subsequently, this N-protected aniline derivative was dissolved in DMF (under $N_2$), cooled to 0° C. and added NaH (1.1 eq). After stirring for 30 min at rt, 2-fluoropyridine was added to the reaction mixture and stirring was continued at 70° C. for 1-3 days. After cooling to rt, aqueous saturated $NaHCO_3$ was added and the mixture extracted with EtOAc. The combined organic phases were dried ($MgSO_4$), filtered and concentrated in vacuo to give the crude product which was purified by preparative LC-MS or by column chromatography to give the desired N-protected N-phenyl-2-aminopyridine. After a reaction step to remove the N-protecting group, using a standard method, the obtained phenyl-pyridin-2-yl-amine was dissolved in acetonitrile (under $N_2$) in a closed vial and added the required halide for the N-alkylation. The reaction mixture was then heated to 100-150° C. for 30-720 min using MW irradiation. After cooling to rt, the crude product could be isolated upon aqueous basic work-up and subsequently purified by preparative LC-MS or, alternatively, by column chromatography and/or recrystallization to give the desired N,N'-disubstituted 2-aminopyridine.

An example of Procedure B, the preparation of [1-(3,4-difluorobenzyl)-1H-pyridin-2-ylidene]-(3,4-difluorophenyl)amine, is shown in Scheme 2.

Scheme 2

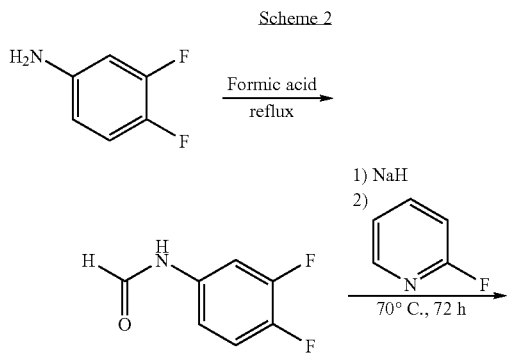

Example 1

(3,4-Difluorobenzyl)-[1-(3,4-difluorobenzyl)-1H-pyridin-2-ylidene (Compound 1)

The title compound was prepared in two steps from 2-fluoropyridine, 3,4-difluorobenzylamine and 3,4-difluorobenzyl bromide as described in Procedure A. Following the second step, the crude product was purified by preparative LC-MS to give the title compound as the formate salt (off-white gum). MS ($ES^+$) m/z 347 ([M+1]$^+$, 100); $^1$H NMR (DMSO-d6) δ 4.53 (s, 2H), 5.48 (s, 2H), 6.72-7.18 (m, 5H), 7.33-7.53 (m, 3H), 7.75-7.83 (m, 1H), 8.12-8.18 (m, 1H), 8.22 (s, 1H).

Example 2

[1-(3,4-Difluorobenzyl)-1H-pyridin-2-ylidene]-(3,4-difluorophenyl)amine (Compound 2)

The title compound was prepared in four steps from 3,4-difluoroaniline, 2-fluoropyridine and 3,4-difluorobenzyl bromide as described in Procedure B. The crude product was purified by preparative LC-MS to give the title compound as the free base (yellowish solid). MS ($ES^+$) m/z 333 ([M+1]$^+$, 100); HR-MS: 333.1008 ([M+1]$^+$, $C_{18}H_{13}F_4N_2$; calc. 333.101485).

Biological Activity

The biological activity of the compounds of the invention may be determined by standard methods known in the art, e.g. as described in Example 16 of WO 2007/110363, in which method the ionic current through small-conductance $Ca^{2+}$-activated $K^+$ channels (SK channels, subtype 3) is recorded using the whole-cell configuration of the patch-clamp technique.

For SK3 inhibitors, a $K_d$ value, defined as the concentration required for decreasing the baseline current to 50% of the

The invention claimed is:

1. A 2-amino-pyridine derivative of Formula I:

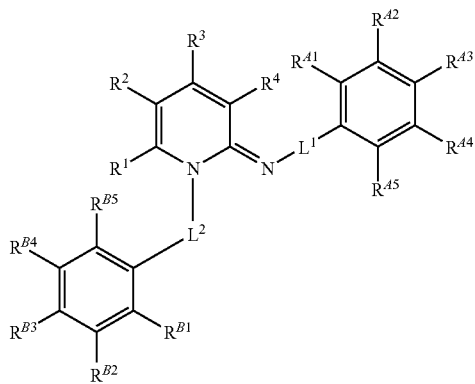

any of its tautomers, or any of its steric isomers or any mixture of its steric isomers, or a pharmaceutically acceptable salt thereof; wherein L$^1$ represents a linking group —[CR'R'']$_n$—; wherein R' and R'', independently of each other, represent hydrogen or alkyl; and n is 0, 1 or 2;

L$^2$ represents a linking group —[CR'''R'''']$_m$—; wherein R''' and R'''', independently of each other, represent hydrogen or alkyl; and m is 1; and R$^1$, R$^2$, R$^3$, R$^4$, R$^{A1}$, R$^{A2}$, R$^{A3}$, R$^{A4}$, R$^{A5}$, R$^{B1}$, R$^{B2}$, R$^{B3}$, R$^{B4}$ and R$^{B5}$, independently of each other, are selected from the group consisting of hydrogen, halo, trifluoromethyl, trifluoromethoxy, cyano, alkyl, hydroxy and alkoxy; provided, however, at least one of R$^1$, R$^2$, R$^3$, R$^4$, R$^{A1}$, R$^{A2}$, R$^{A3}$, R$^{A4}$, R$^{A5}$, R$^{B1}$, R$^{B2}$, R$^{B3}$, R$^{B4}$ and R$^{B5}$ is not hydrogen; and if n is 1, then R$^{A3}$ and R$^{B3}$ are not both bromo; or then R$^2$ is not methyl and R$^{B2}$ is not trifluoromethyl.

2. The 2-amino-pyridine derivative of claim 1, any of its tautomers, or any of its steric isomers or any mixture of its steric isomers, or a pharmaceutically acceptable salt thereof, wherein L$^1$ represents a linking group —[CR'R'']$_n$—; wherein R' and R'', independently of each other, represent hydrogen or alkyl; and n is 0.

3. The 2-amino-pyridine derivative of claim 1, any of its tautomers, or any of its steric isomers or any mixture of its steric isomers, or a pharmaceutically acceptable salt thereof, wherein L$^1$ represents a linking group —[CR'R'']$_n$—; wherein R' and R'', independently of each other, represent hydrogen or alkyl; and n is 1.

4. The 2-amino-pyridine derivative of claim 1, any of its tautomers, or any of its steric isomers or any mixture of its steric isomers, or a pharmaceutically acceptable salt thereof, wherein R$^1$, R$^2$, R$^3$, and R$^4$, independently of each other, are selected from the group consisting of hydrogen, halo, trifluoromethyl, trifluoromethoxy, cyano, hydroxyl, and alkoxy; and R$^{A1}$, R$^{A2}$, R$^{A3}$, R$^{A4}$, R$^{A5}$, R$^{B1}$, R$^{B2}$, R$^{B3}$, R$^{B4}$ and R$^{B5}$, independently of each other, are selected from the group consisting of hydrogen, halo, trifluoromethyl, trifluoromethoxy, cyano, alkyl, hydroxy and alkoxy.

5. The 2-amino-pyridine derivative of claim 4, any of its tautomers, or any of its steric isomers or any mixture of its steric isomers, or a pharmaceutically acceptable salt thereof, wherein R$^1$, R$^2$, R$^3$ and R$^4$ all represent hydrogen; and R$^{A1}$, R$^{A2}$, R$^{A3}$, R$^{A4}$, R$^{A5}$, R$^{B1}$, R$^{B2}$, R$^{B3}$, R$^{B4}$ and R$^{B5}$, independently of each other, are selected from the group consisting of hydrogen, halo, trifluoromethyl, trifluoromethoxy, cyano, alkyl, hydroxy and alkoxy.

6. The 2-amino-pyridine derivative of claim 1, which is (3,4-difluorobenzyl)-[1-(3,4-difluorobenzyl)-1H-pyridin-2-ylidene; or

[1-(3,4-difluorobenzyl)-1H-pyridin-2-ylidene]-(3,4-difluorophenyl)amine;

any of its tautomers, or any of its steric isomers or any mixture of its steric isomers, or a pharmaceutically acceptable salt thereof.

7. A pharmaceutical composition, comprising a therapeutically effective amount of the 2-amino-pyridine derivative of claim 1, or any of its tautomers or any of its steric isomers or any mixture of its steric isomers, or a pharmaceutically acceptable salt thereof, together with at least one pharmaceutically acceptable carrier, excipient or diluent.

* * * * *